US011866455B2

(12) United States Patent
Soto Gonzalez et al.

(10) Patent No.: US 11,866,455 B2
(45) Date of Patent: Jan. 9, 2024

(54) GOLD(III) COMPLEX, A CONJUGATE OF THE GOLD(III) COMPLEX, A PHARMACEUTICAL COMPOSITION COMPRISING THE GOLD(III) COMPLEX AND USES AND A PROCESS FOR PREPARING THE GOLD(III) COMPLEX

(71) Applicants: UNIVERSIDAD DE ALMERIA, Almeria (ES); FUNDACION PRIVADA INSTITUTO DE SALUD GLOBAL BARCELONA, Barcelona (ES)

(72) Inventors: Sara Maria Soto Gonzalez, Terrassa (ES); Carlos Ratia Loncan, Barcelona (ES); Virginio Cepas Lopez, Sabadell (ES); Yuly Lopez Cubillos, Barcelona (ES); Fernando Lopez Ortiz, Almeria (ES); Maria Jose Iglesias Valdes-Solis, Almeria (ES); Raquel Maria Gonzalez Soengas, Retamar (ES)

( * ) Notice: Subject to any disclaimer, the term of this patent is extended or adjusted under 35 U.S.C. 154(b) by 356 days.

(21) Appl. No.: 17/050,512

(22) PCT Filed: Apr. 29, 2019

(86) PCT No.: PCT/EP2019/060879
§ 371 (c)(1),
(2) Date: Oct. 26, 2020

(87) PCT Pub. No.: WO2019/211222
PCT Pub. Date: Nov. 7, 2019

(65) Prior Publication Data
US 2021/0188886 A1    Jun. 24, 2021

(30) Foreign Application Priority Data
May 3, 2018   (EP) ..................... 18382305

(51) Int. Cl.
| | |
|---|---|
| *C07F 9/6558* | (2006.01) |
| *A61P 31/04* | (2006.01) |
| *A01N 57/02* | (2006.01) |
| *A01N 57/08* | (2006.01) |
| *C07F 9/54* | (2006.01) |
| *C07F 9/572* | (2006.01) |
| *C07F 9/59* | (2006.01) |

(52) U.S. Cl.
CPC ............ *C07F 9/6558* (2013.01); *A01N 57/02* (2013.01); *A01N 57/08* (2013.01); *A61P 31/04* (2018.01); *C07F 9/5463* (2013.01); *C07F 9/572* (2013.01); *C07F 9/59* (2013.01)

(58) Field of Classification Search
CPC ............ C07F 9/655345; C07F 9/6558; C07F 9/5463
See application file for complete search history.

(56) References Cited

PUBLICATIONS

Glisic, BD, et al.; Gold complexes as antimicrobial agents: an overview of different biological activities in relation to the oxidation state of the gold ion and the ligand structure; Dalton Trans. 43, 5950-5969; 2014; The Royal Society of Chemistry.

Oña-Burgos, P, Fernández, I, Roces, L, Torre-Fernández, L, García-Granda, S, López-Ortiz, F; An Unprecedented Phosphinamidic Gold(III) Metallocycle: Synthesis via Tin(IV) Precursors, Structure, and Multicomponent Catalysis; Organometallics, 28, 1739-1747; 2009; American Chemical Society.

Belmonte Sánchez, E, et al.; Cycloaurated Phosphinothioic Amide Complex as a Precursor of Gold(I) Nanoparticles: Efficient Catalysts for A3 Synthesis of Propargylamines under Solvent-Free Conditions; Organometallics 36, 1962-1973; 2017; ACS Publications, American Chemical Society.

Ronconi, L et al., Perspective Gold(III)-Dithiocarbamato Anticancer Therapeutics: Learning from the Past, Moving to the Future; Adv. Anticancer Agents Med. Chem. 2, 130-172; 2013; Bentham Science Publishers.

Borhade, S; Synthesis, Characterisation and Antimicrobial Activity of Gold (III) with 2-Chloroquinoline-3-Carbaldehyde Thiosemicarbazide {1-((2-Chloroquinoline-3-YL) Methylene Thiosemicarbazide (2-Chloro-QAT); Int. Res. J. Pharm. 3, 189-193; 2012; International Research Journal of Pharmacy.

Al-Khodir, F.A.I, Refat, M.S.; Spectroscopic Elaboration and Structural Characterizations of New Fe(III), Pd(II), and Au(III) Ampicillin Complexes: Metal-Antibiotic Ligational Behaviors; J. Pharm. Innov. 10, 335-347; 2015.

Glisic, BD., et al.; Synthesis, structural characterization and biological evaluation of dinuclear goldIJIII) complexeswith aromatic nitrogen-containing ligands: antimicrobial activity in relation to the complex nuclearity; MedChemComm, 7, 1356-1366; 2016.

Pintus, A, et al.; [Au(pyb-H)(mnt)]: A novel gold(III) 1,2-dithiolene cyclometalated complex with antimicrobial activity (pyb-H = C-deprotonated 2-benzylpyridine; mnt = 1,2-dicyanoethene-1,2-dithiolate); J. Inorg. Biochem. 170, 188-194; 2017.

Mignani, SM, et al.; Original Multivalent Gold(III) and Dual Gold(III)-Copper(II) Conjugated Phosphorus Dendrimers as Potent Antitumoral and Antimicrobial Agents; Mol. Pharmaceutics, 14, 4087-4097; 2017.

Savic, ND, et al.; A comparative antimicrobial and toxicological study of gold(III) and silver(I) complexes with aromatic nitrogen-containing heterocycles: synergistic activity and improved selectivity index of Au(III)/Ag(I) complexes mixture; RSC Advances 6, 25 13193-13206; 2016.

(Continued)

*Primary Examiner* — Laura L Stockton
(74) *Attorney, Agent, or Firm* — Eugenio J. Torres-Oyola; Victor M. Rodriguez-Reyes; Rafael Rodriguez-Muriel

(57) ABSTRACT

A gold(III) complex, a conjugate of the gold(iII) complex, a pharmaceutical composition comprising the gold(III) complex and uses and a process for preparing the gold(III) complex. The complex comprises a group of (S^C)-cyclometallated gold(III) complexes containing a 1,1-dithio ligand, which exhibit antibacterial activity against multiresistant microorganisms or against biofilm activity or biofilm disruption. The gold(III) complex has efficacy against a variety of microorganisms and low toxicity.

6 Claims, 9 Drawing Sheets

(56) References Cited

PUBLICATIONS

Radulovic, NS, et al.; Water-soluble gold(III) complexes with N-donor ligands as potential immunomodulatory and antibiofilm agents; Polyhedron 141, 164-180; 2018.

Shaik, N et al.; Synthesis of Apoptosis-Inducing Iminophosphorane Organogold(III) Complexes and Study of Their Interactions with Biomolecular Targets; Inorg. Chem. 48, 1577-1587; 2009.

L. Vela et al.; Iminophosphorane-organogold(III) complexes induce cell death through mitochondrial ROS production; J. Inorg. Biochem., 105, 1306; 2011.

Parish, RV et al.; Integration of antennas with sun-tracking solar pannels; Inorg. Chem., 35, 1659; 1996.

Flower, KR, et al.; Isolation of 1,4-Li2—C6H4 and its reaction with [(Ph3P)AuCl]; Dalton Transactions 39, 3509-3520; 2010.

Pena-Lopez, M, et al.; Palladium-catalyzed cross-coupling reactions of organogold(I) phosphanes with allylic electrophiles; Org. Biomol. Chem., 10, 1686-1694; 2012.

Espinet, P et al.; [2,4,6-Tris(trifluoromethyl)phenyl]gold(I) and -gold(III) Complexes; Organometallics, 19, 290-295; 2000.

Kilpin, K.J. et al.; Cycloaurated triphenylphosphine-sulfide and -selenide; Dalton Trans. 39, 1855-1864; 2010.

Vicente, J, et al.; Gold(I) and Gold (III) ortho-Nitrophenyl Complexes, Crystal and Molecular structure of ortho-Nitrophenyltriphenylarsinegold(I); Organometallic Chemistry, 309, 3689-378; 1986.

Hofer, M., et al.; A Neutral Gold(III)-Boron Transmetalation; Organometallics 33, 1328-1332; 2014.

Winston, MS, et al.; Photoinitiated Oxidative Addition of CF3I to Gold(I) and Facile ArylCF3 Reductive Elimination; American Chemical Society, 136, 7777-7782; 2014.

Price, GA, et al.; First structurally confirmed example of the formation of a gold(III) carbon bond via transmetallation with a boroxine; Dalton Transactions, 40, 11696-11697; 2011.

GOLD(III) COMPLEX, A CONJUGATE OF THE GOLD(III) COMPLEX, A PHARMACEUTICAL COMPOSITION COMPRISING THE GOLD(III) COMPLEX AND USES AND A PROCESS FOR PREPARING THE GOLD(III) COMPLEX

TECHNICAL FIELD

The present invention is directed, in general, to pharmaceutical compounds. In particular, the invention relates to a gold(III) complex, having formula (I), to be used as antibacterial and/or antibiofilm agents.

BACKGROUND OF THE INVENTION

The rapid emergence of bacteria and other microorganisms is jeopardizing the efficacy of antibiotics, which have transformed medicine and saved millions of human and animal lives. Multiresistant bacteria are a global threat, estimated to cause 700,000 deaths worldwide each year. By the year 2050, 10 million people will die every year in the world from bacterial infections. They would exceed 1.8 million deaths from cancer. Recently, WHO has identified a group of multiresistant bacteria that are able to "escape" from the biocidal action of all known antibiotics and represent new paradigms in pathogenesis, transmission and resistance bacteria of particular concern include *Enterococcus faecium, Staphylococcus aureus, Klebsiella pneumoniae, Acinetobacter baumannii, Pseudomonas aeruginosa* (PAO) and *Enterobacteriaceae* species.

Gold(I) complexes have historically been studied as antimicrobial agents. A relevant example is the gold(I) complex auranofin, a drug initially approved as an antirheumatic agent, which also possesses potent antibacterial activity.

On the contrary, although gold(III) complexes have been intensively investigated as possible antitumor agents due to their similarities with platinum(II) complexes, until recently there were few references on their antibacterial activity. In recent years, the serious threat of resistant "superbugs" led to the evaluation of these antitumor drugs as well as antimicrobials, demonstrating antimicrobial activity against a wide range of pathogenic bacteria (Glisic, BD, et al., Dalton Trans. 2014, 43, 5950). The stabilization of the +3 oxidation state is of prime importance to observe any type of biological activity. Otherwise, the metal center could be reduced, causing the formation of Au(0) and inactivation of the complex. In this regard, the advantage of organometallic cyclometalated gold compounds is their greater stability.

Taking into account the promising biological profile of cycloaurated complexes, the inventors of present invention have recently initiated an investigation into the rational design of a novel class of Au(III) complexes in which the metal center was integrated into a C,Y-metallacycle (Y=S, O). Using this concept, the inventors previously reported the synthesis of (O^C)-cycloaurated complexes based on an ortho-substituted phosphinic (Oña-Burgos, P, Fernández, I, Roces, L, Torre-Fernández, L, García-Granda, S, López-Ortiz, F, Organometallics 2009, 28, 1739-1747) or thiophosphinic amide frameworks (Sánchez, EB, Iglesias, MJ, el Hajjouji, H, Roces, L, García-Granda, S, Villuendas, P, Urriolabeitia, EP, López-Ortiz, F, Organometallics 2017, 36, 1962-1973), respectively, through tin(IV)-gold(III) transmetalation of the corresponding ortho chlorodimethylstannyl derivatives.

Besides that, therapeutic applications of gold(III) complexes focus primarily on anticancer properties (Ronconi, L et al., Adv. Anticancer Agents Med. Chem. 2013, 2, 130-172). With the rise of the threat of antibiotic resistance, increasing attention is being given to the antimicrobial properties of this compound class.

Gold(III) complexes tested for antimicrobial activity are either simple salts of Au(III) (e.g., tetrachlorides, carboxylates, etc. Borhade, S, Int. Res. J. Pharm. 2012, 3, 189-193. Al-Khodir, F.A.I, Refat, M.S. J. Pharm. Innov. 2015, 10, 335-347. Glisic, B D., et al MedChemComm 2016, 7, 1356-1366) or cyclometalates involving C^N chelating ligands, usually aromatic nitrogen-containing heterocycles such as 2,2'-bipyridine, 2,2':6',2"-terpyridine, quinoline, 1,10-phenanthroline, etc. (Glisic, B D., Djuran, M I, Dalton Trans. 2014, 43, 5950-5969. Pintus, A, et al. J. Inorg. Biochem. 2017, 170, 188-194. Mignani, S M, et al. Mol. Pharmaceutics 2017, 14, 4087-4097.

Very recently, the behavior of complexes of NHet·AuCl$_3$ (NHet=pyrazine, pyrimidine, piridazine, quinoxaline and phenazine) (Savic, N D, et al. RSC Advances 2016, 6, 13193-13206) and C^N-stabilized gold(III) cyclometalates (Radulovic, N S, et al. Polyhedron 2018, 141, 164-180) as antibiofilm agents has been reported.

Concerning gold(III) complexes containing a dithiocarbamate moiety, it has been described that the corresponding cycloaurates derived from phosphazenes showed in vitro anticancer activity against HeLa human cervical carcinoma and Jurkat-T acute lymphoblastic leukemia cells (Shaik, N et al. Inorg. Chem. 2009, 48, 1577-1587. L. Vela et al. J. Inorg. Biochem. 2011, 105, 1306).

Apart from that, there is one report in which C^N-stabilized gold(III) cyclometalates (three examples involving the chelating ligand 2-((dimethylamino)methyl)phenyl) bearing a dithiocarbamate ligand) were investigated as antibacterial and antifungal agents. The complexes were less active than the control antibiotics, ciprofloxacin and amphotericin (Parish, RV, Inorg. Chem. 1996, 35, 1659). There are no precedents on the antimicrobial and antibiofilm therapeutic properties of gold(III) complexes of formula (I) in which the Au(III) is part of a C—C—P—S—Au metallacycle.

BRIEF DESCRIPTION OF THE INVENTION

An object of the present disclosure is to provide stable cyclometalated gold(III) complexes having efficacy against a variety of microorganisms and low toxicity.

A group of (S^C)-cyclometalated gold(III) complexes containing a 1,1-dithio ligand, as represented in formula (I), which exhibit antibacterial activity against multiresistant microorganisms in planktonic or biofilm state, especially *S. aureus, S. maltophilia*, PAO, and *H. influenziae* (i.e. avoid the formation of biofilms of bacteria or eliminate those already formed). Thus, a new therapeutic tool to treat the infections caused by these bacteria is provided.

In addition, the compounds of formula (I) are not only highly active, as determined by in vitro tests, but are also highly stable under physiological conditions so they are expected to maintain their antibacterial activity in vivo in the same way.

Additionally, in vitro and in vivo assays show low toxicity of the compounds of formula (I).

According to a first aspect, the present disclosure relates to a gold(III) complex having formula

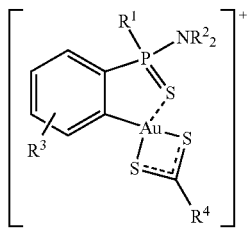

wherein:
- $R^1$ is independently selected from aryl and amine;
- $R^2$ is independently selected from alkyl and cycloalkyl;
- $R^3$ is independently selected from hydrogen, halogen, nitro, cyano, alkyl, alkyloxy, alkylamino, aminodialkyl, hydroxyalkyl, trialkylsilyl, aryldialkylsilyl, alkylthio, cycloalkyl, aryl, heterocycle, polycycle, amino acid, peptide and carbohydrate derivative; and
- $R^4$ is independently selected from alkyl, cycloalkyl, alkylalkoxy, alkylamino, dialkylamino, alkylthio, trialkylphosphino, dialkylarylphosphino, alkyldiarylphosphino, triarylphosphino aryl, heterocycle, polycycle, amino acid, peptide and carbohydrate derivative.

In an embodiment, binuclear complexes analogous to (I) are included. In this regard, a complex with two type (I) structures connected by a piperazine ring is used. Likewise, homo and heterobinuclear complexes can be used. They include complexes prepared using a $R^4$ substitute that has coordination positions to another metal.

In an embodiment, the radicals that can be used are:
- $R^1$=phenyl, and $N(R^2)_2$, being $R^2$=dialkyl (i.e. $N(R^2)_2$= $N(^iPr)_2$, $N(Et)_2$, piperazine;
- $R^3$=hydrogen;
- $R^4$=aliphatic amine such as $NMe_2$, $NEt_2$, $N(CH_2Ph)_2$, pyrrolidyl, piperidinyl, and azepanyl links, or heterocyclical including piperazinyl or morpholinyl; and
- $R^4$ as ligand for dinuclear complexes, for example piperazine, i.e. a homonuclear complex. The amine can easily be changed to include a second electron donor atom (the simplest way is to use amines with heterocyclic systems such as pyridine or azoles. That leaves a second position to coordinate other metals, for example, AuCl-L (L=$Ph_3P$, tetrahydrothiophene), $AuCl_3$ and copper salts.

Another aspect of the present invention relates to a conjugate comprising the cited gold(III) complex of formula (I) and at least one carrier, preferably a pharmaceutical carrier.

Another aspect of the present invention relates to a pharmaceutical composition comprising the cited gold(III) complex of formula (I) or the above-mention conjugate and at least one pharmaceutically acceptable excipient.

In an embodiment, the gold(III) complex, the conjugate or the pharmaceutical composition is used in the manufacture of a medicament, for example for the treatment of a microbial infection.

In another embodiment, the gold(III) complex, the conjugate or the pharmaceutical composition is used as a medicament in the treatment and/or prevention of bacterial infections caused by multiresistant bacteria or other microorganisms.

In another embodiment, the gold(III) complex, the conjugate or the pharmaceutical composition is used to inhibit biofilm formation or development, to eliminate mature biofilms and/or to reduce the biofilm biomass.

Another aspect of the present invention relates to a process for preparing the gold(III) complex of formula (I), comprising reacting a compound of formula (V)

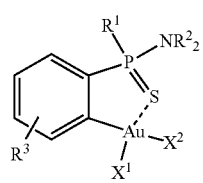

with a compound of formula (VI)

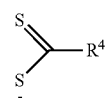

and subsequent formation of a pharmaceutically stable salt or solvate of the resulting complex by treatment with an organic or inorganic acid or their corresponding salts, wherein:
- $X^1$ is independently selected from halogen, hydroxide or acetoxy;
- $X^2$ is independently selected from halogen, hydroxide or acetoxy;
- $R^1$ is independently selected from aryl and amine;
- $R^2$ is independently selected from alkyl and cycloalkyl;
- $R^3$ is independently selected from hydrogen, halogen, nitro, cyano, alkyl, alkyloxy, alkylamino, aminodialkyl, hydroxyalkyl, trialkylsilyl, aryldialkylsilyl, alkylthio, cycloalkyl, aryl, heterocycle, polycycle, amino acid, peptide and carbohydrate derivative; and
- $R^4$ is independently selected from alkyl, cycloalkyl, alkylalkoxy, alkylamino, dialkylamino, alkylthio, trialkylphosphino, dialkylarylphosphino, alkyldiarylphosphino, triarylphosphino aryl, heterocycle, polycycle, amino acid, peptide and carbohydrate derivative.

BRIEF DESCRIPTION OF THE DRAWINGS

The previous and other advantages and features will be more fully understood from the following detailed description of embodiments, with reference to the attached figures, which must be considered in an illustrative and non-limiting manner, in which.

DETAILED DESCRIPTION OF PREFERRED EMBODIMENTS

Figure 1:
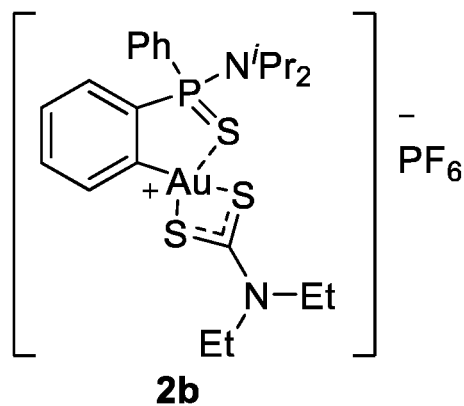
FIG. 1 shows the structure of complex 2b

Present invention relates in a first embodiment to a gold(III) complex having formula (I):

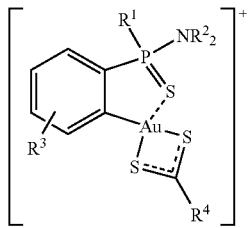

I wherein:
- $R^1$ is independently selected from aryl and amine
- $R^2$ is independently selected from alkyl and cycloalkyl
- $R^3$ is independently selected from hydrogen, halogen, nitro, cyano, alkyl, alkyloxy, alkylamino, aminodialkyl, hydroxyalkyl, trialkylsilyl, aryldialkylsilyl, alkylthio, cycloalkyl, aryl, heterocycle, polycycle, amino acid, peptide and carbohydrate derivative
- $R^4$ is independently selected from alkyl, cycloalkyl, alkylalkoxy, alkylamino, dialkylamino,alkylthio, trialkylphosphino, dialkylarylphosphino, alkyldiarylphosphino, triarylphosphino, aryl, heterocycle, polycycle, amino acid, peptide and carbohydrate derivative.

The compounds of formula (I) contain a positive charge and can form salts with organic or inorganic acids. Therefore, pharmaceutically acceptable salts of the compounds of formula (I) are also included within the scope of the invention. Any reference to a compound of formula (I) throughout the description includes a reference to any pharmaceutically acceptable salt of such compound of formula (I). The term "pharmaceutically acceptable salts", as used herein, encompasses any salt without any limitation on the salt that can be used, provided that these are acceptable for administration to a patient. For example, pharmaceutically acceptable salts include chloride, bromide, malonate, pyruvate, etc. Hexafluorophosphate is preferred.

In another embodiment, the invention relates to compounds of formula (I) having a minimum inhibitory concentration (MIC) of 0.125-0.5 mg/L for S. aureus, of 2-4 mg/L for S. maltophilia and of 1-2 mg/L for H. influenziae, being lower than the MICs of other antibiotics used in the treatment infections caused by these microorganisms, as described in example 2 for S. aureus. As shown in the example, the compounds of the present invention showed high antibacterial activity against a series of strains resistant to methicillin, clindamycin, erythromycin, ciprofloxacin, with values of minimum inhibitory concentration (MIC) equal to or less than 0.5 mg/L for all the compounds tested.

Therefore, present invention also provides a compound of formula (I) or any pharmaceutically acceptable salt for its use in the manufacture of a medicament for the treatment and/or prevention of a microbial infection.

In another embodiment, the present invention relates to the use of a compound of formula (I) as an antimicrobial agent for the treatment of a human or animal patient afflicted with an infection by multiresistant microorganisms, including the administration to said patient of an effective amount of a pharmaceutical composition containing the compound of formula (I). As shown in example 3, compounds of formula (I) have resulted in low-null toxicity in mice at doses greater than 5 mg/kg in weight, much higher than the concentration at which it is active.

In another embodiment, due to the high activity of the compounds of formula (I) against multiresistant microorganisms, these compounds can be used in combination with other antimicrobials, typically broad spectrum antibiotics, to thereby enhance the antimicrobial efficacy of the therapy. Compounds of formula (I) can be combined with any type of antimicrobial agent used in therapy, as (but not limited to) vancomycin, daptomycin, fosfomycin, ciprofloxacin or imipenem.

The combination of compounds of formula (I) with an additional antimicrobial agent can be achieved by administering both substances as a fixed dose combination in pharmaceutical dosage form or, alternatively, both drugs can be administered independently, according to a therapeutic combination regimen.

Alternatively, the compound of formula (I) can be combined with another antibacterial agent by covalently bonding both compounds to form a single molecule. For example, the compound of formula (I) can be linked to an antibacterial compound of fluoroquinolone, carbapenemic or penicillin derivative, according to formulas (II-IV).

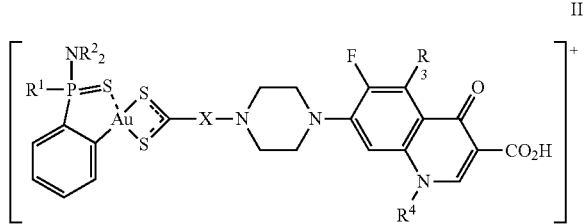

II

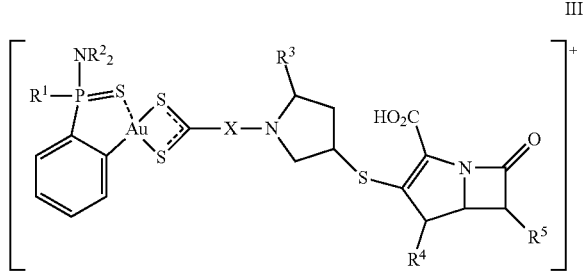

III

-continued

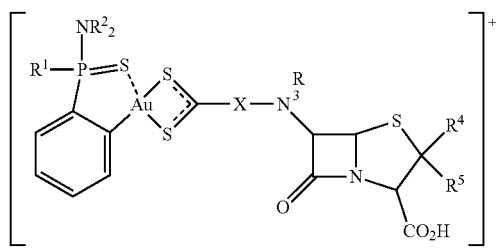

IV

In another embodiment, the biosynthetic pathways involved in the antibacterial activity of compound of formula (I) are studied. Their possible role in the interaction with intracellular proteins and enzymes, in the catalysation of various intracellular processes, in the ability of mutating the bacterial DNA and/or in the overexpression or repression of genes and the consequent proteins is studied using proteomics, genomics and microscopic approaches.

In another embodiment, present invention relates to a pharmaceutical composition comprising a compound of formula (I) and at least one acceptable pharmaceutical excipient or carrier.

Another embodiment of the present invention relates to the use of the compounds of the present invention to inhibit the formation or development of biofilm, eliminating existent biofilms, and reducing the biofilm biomass.

A method for inhibiting biofilm formation is also proposed, including exposing formed biofilms to an effective amount of the compound of the invention for eradication. Thus, as shown in example 4, compounds of formula (I) have minimal Biofilm Inhibition Concentrations (MBIC) lower than antibiotics used in the treatment of these infections as in the case of *S. aureus*.

In some embodiments, the compound of the invention is impregnated or deposited on the surface susceptible to biofilm formation.

The surface can be the surface of a medical instrument such as: surgical equipment, implants or prostheses, catheters (urinary or venous), stents, pacemakers, dialysis equipment, heart valves and medical fixation instruments (plates, screws, nails . . . ).

Another embodiment of the present invention relates to a process for the preparation of a compound of formula (I) (as defined above) which comprises reacting a compound of formula (V)

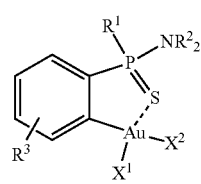

V wherein:

$X^1$ is independently selected from halogen, hydroxide or acetoxy $X^2$ is independently selected from halogen, hydroxide or acetoxy $R^1$ is independently selected from aryl and amine $R^2$ is independently selected from alkyl and cycloalkyl $R^3$ is independently selected from hydrogen, halogen, nitro, cyano, alkyl, alkoxyalkyl, aminoalkyl, aminodialkyl, hydroxyalkyl, trialkylsilyl, aryldialkylsilyl, alkylthio, cycloalkyl, aryl, heterocycle, polycycle, amino acid, peptide and carbohydrate derivative with a compound of formula (VI)

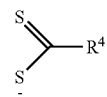

VI wherein:

$R^4$ is independently selected from alkyl, cycloalkyl, alkylalkoxy, alkylamino, dialkylamino, alkylthio, trialkylphosphino, dialkylarylphosphino, alkyldiarylphosphino, triarylphosphino aryl, heterocycle, polycycle, amino acid, peptide and carbohydrate derivative, and subsequent formation of a pharmaceutically stable salt or solvate of the resulting complex by treatment with an organic or inorganic acid or their corresponding salts.

The procedure can be represented according to Scheme I:

The present invention also relates to a method for the preparation of compound V, consisting of the ortho-metallation of a thiophosphinic or thiophosphonic amide framework, followed by transmetallation with a gold(I) salt and oxidation to gold(III), as represented in Scheme II:

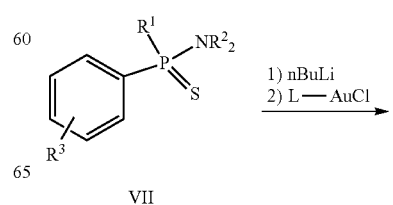

VII

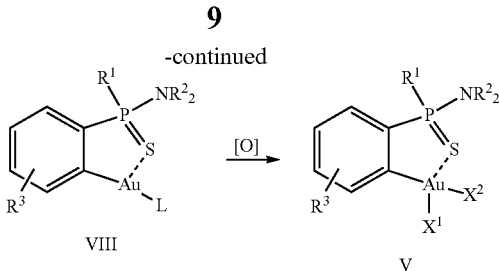

wherein:

L is independently selected from a tertiary phosphine (Flower, K R, et al. Dalton Transactions 2010, 39, 3509-3520), a tertiary arsine (Pena-López, M, et al Org. Biomol. Chem. 2012, 10, 1686-1694) or a thioether (Espinet, P, Organometallics, 2000, 19, 290-295).

It should be mentioned that the derivative of compound V were $R^1$=$NEt_2$, $N(R^2)_2$=$NEt_2$, $R^3$=H, $X^1$=$X^2$=Cl has been already synthesized by Kilpin, K. J. et al. (Dalton Trans. 2010, 39, 1855-1864) via Hg(II)/Au(III) exchange, i.e., a procedure different from the method described in the present patent application (Sn(IV)/Au(III) exchange).

The oxidant agent is selected from $X_2$ (Viente, J, Arcas, A, Marc, M, J. Organomet. Chem 1986, 309, 3689-378), $PhIX_2$ (Hofer, M., Gomez-Bengoa, E, Nevado, C, Organometallics 2014, 33, 1328-1332) or $CF_3I$ (Winston, M S, Wolf, W J, Toste, F D, J. Am. Chem. Soc. 2014, 136, 7777-7782).

Alternatively, complex (V) can be prepared by boron/Au(III) metathetical reactions using the corresponding ortho borinated derivative of phosphinothioic amide VII (Price, G A, et al. Dalton Trans., 2011, 40, 11696-11697).

The compounds of the present invention, as well as the intermediates, can be prepared by the methods described herein or small variations thereof, as well as by alternative methods.

Further aspects of the invention relate to the stability of the compounds of formula (I) in physiological conditions and in the presence of classical reducing agents and human serum albumine.

EXAMPLES

The following examples have been included to further describe protocols for the synthesis and evaluation of the gold(III) complexes. It should be noted that these examples have been included for illustrative purposes, and are not intended to limit the scope of the invention.

Synthesis of Gold(III) Complexes

All reactions were carried out under inert atmosphere, in previously dried Schlenks. $CH_3CN$ was distilled in the presence of $P_2O_5$ and degassed before use. Commercial reagents were used as received.

Synthesis of complexes 2: To a solution of Au(III) complex 1 (0.20 mmol) in $CH_3CN$ (6 mL), the corresponding dithiocarbamate salt was added (0.20 mmol). The reaction mixture was stirred at rt for 12 h. After addition of aqueous saturated potassium hexafluorophosphate, the resulting solid was filtered and the residue was washed with water and diethyl ether to afford complexes 2 as bright yellow solids. The most relevant analytical data of selected gold complexes (III) are presented in Table 1.

NMR Experiments

NMR spectra were obtained on a Bruker Avance III HD 300 ($^1$H 300.13 MHz; $^{13}$C 75.47 MHz; $^{31}$P 121.49 MHz) and Bruker Avance III HD 500 ($^1$H 500.13 MHz; $^{13}$C 125.76 MHz; $^{31}$P 202.46 MHz). Chemical shifts are given in ppm using tetramethylsilane (TMS) for $^1$H and $^{13}$C as internal standards and 85% $H_3PO_4$ for $^{31}$P as external standard. $^1$H, $^1$H{$^{31}$P} and $^{31}$P NMR spectra were acquired from all reaction crudes in $CDCl_3$ or $CD_3CN$ as solvent. The following abbreviations are used to indicate the multiplicity of signal: s—singlet, d—doublet, t—triplet, q—quartet and sep—septet.

All the NMR spectra supported the structures of the synthesized compounds.

Mass Spectroscopy

High Resolution Mass Spectra (HRMS) were recorded on an Agilent Technologies LC/MSD-TOF and HP 1100 MSD spectrometer using electrospray ionization.

The auracyclic complexes 2 have also been characterized by electrospray ionization mass spectrometry (ESI-MS), showing a strong peak due to the gold cation. Calculated isotopic clusters were in excellent agreement with the experimental ones.

TABLE 1

Figure 2:
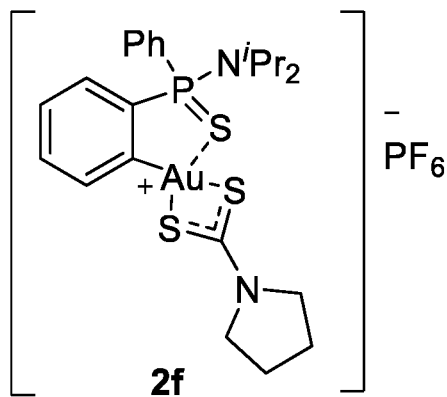
FIG. 2 shows the structure of complex 2f

| Structure | Name/Analytical data |
|---|---|
| FIG. 1 | [Gold(III) 2-((diisopropylamino)(phenyl)phosphorothioyl)phenyl) (diethyldithiocarbamate)] hexafluorophosphate<br>$^1$H NMR (300 MHz, $CDCl_3$) δ 1.20 (d, $^3J_{PH}$ 6.8 Hz, 6H), 1.30 (d, $^3J_{PH}$ 6.8 Hz, 6H), 1.37 (q, $^3J_{HH}$ 7.0 Hz, 6H), 1.32 (d, $^3J_{PH}$ 6.8 Hz, 6H), 3.66-3.85 (m, 6H), 7.36 (ddd, 1H, $^3J_{HH}$ 7.8 Hz, $^4J_{PH}$ 3.6 Hz, $^4J_{HH}$ 1.2 Hz), 7.47 (tt, 1H, $^3J_{HH}$ 7.4 Hz, $^5J_{PH}$ 1.7 Hz, $^4J_{HH}$ 1.7 Hz), 7.54-7.70 (m, 4H), 7.77 (ddd, 1H, $^3J_{PH}$ 10.2 Hz, $^3J_{HH}$ 7.6 Hz, $^4J_{HH}$ 1.6 Hz), 7.98-8.32 (m, 2H) ppm. $^{13}$C NMR (75 MHz, $CDCl_3$) δ 12.3, 12.4, 23.0 (d, $^3J_{PC}$ 3.0 Hz), 23.3 (d, $^3J_{PC}$ 3.3 Hz), 50.7 (d, $^2J_{PC}$ 3.2 Hz), 127.4 (d, $^1J_{PC}$ 101.8 Hz), 128.5 (d, $^3J_{PC}$ 11.9 Hz), 129.6 (d, $^3J_{PC}$ 13.7 Hz), 132.4 (d, $^3J_{PC}$ 17.0 Hz), 131.7 (d, $^2J_{PC}$ 13.2 Hz), 133.4 (d, $^2J_{PC}$ 11.8 Hz), 134.7 (d, $^4J_{PC}$ 3.1 Hz), 135.3 (d, $^4J_{PC}$ 3.5 Hz), 138.6 (d, $^1J_{PC}$ 124.1 Hz), 143.7 (d, $^2J_{PC}$ 28.0 Hz), 194.5 ppm. $^{31}$P-NMR (121 MHz, $CDCl_3$) δ −143.6 (h, $^1J_{PF}$ 712.3 Hz), 76.4 ppm.<br>HRMS (ESI$^+$) [M]$^+$ calcd. for $C_{21}H_{29}AuN_2PS_3$, 661.1023; found, 661.1019. |
| FIG. 2 | [Gold(III) 2-((diisopropylamino)(phenyl)phosphorothioyl)phenyl) (pirrolidin-1-dithiocarbamate)] hexafluorophosphate<br>$^1$H NMR (300 MHz, $CDCl_3$) δ 1.23 (d, $^3J_{PH}$ 6.8 Hz, 6H), 1.32 (d, $^3J_{PH}$ 6.8 Hz, 6H), 2.16-2.23 (m, 4H), 3.65-3.90 (m, 4H), 3.65-3.90 (m, 6H), 7.33 (ddd, $^3J_{HH}$ 7.8 Hz, $^3J_{PH}$ 3.6 Hz, $^4J_{HH}$ 1.7 Hz, 1H), 7.46 (ttt, $^3J_{HH}$ 7.5 Hz, $^3J_{PH}$ 7.5 Hz, $^4J_{HH}$ 1.7 Hz, 1H), 7.54-7.79 (m, 5H), 8.02-8.17 (m, 2H) ppm. $^{13}$C NMR (75 MHz, $CDCl_3$) 23.1 (d, $^3J_{PC}$ 3.1 Hz), 23.4 (d, $^3J_{PC}$ 3.4 Hz), 24.0, 24.2, 50.7 (d, $^2J_{PC}$ 3.3 Hz), 51.0, 51.6, 127.4 (d, $^1J_{PC}$ 101.7 Hz), 128.4 (d, $^3J_{PC}$ 12.0 Hz), 129.6 (d, $^3J_{PC}$ 13.6 Hz), 132.6 (d, $^3J_{PC}$ 16.7 Hz), 133.1 (d, $^2J_{PC}$ 12.2 Hz), 133.4 (d, $^2J_{PC}$ 11.8 Hz), 134.7 (d, $^4J_{PC}$ 3.1 Hz), 135.3 (d, $^4J_{PC}$ |

TABLE 1-continued

Figure 3:
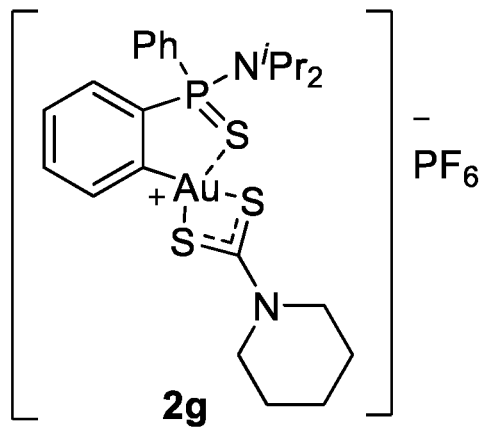
FIG. 3 shows the structure of complex 2g
Figure 4:
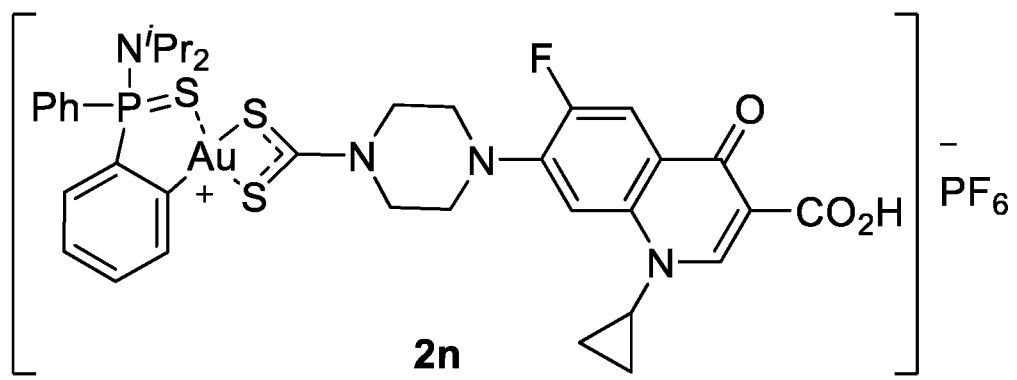
FIG. 4 shows the structure of complex 2n

| Structure | Name/Analytical data |
|---|---|
| | 3.6 Hz), 138.4 (d, $^1J_{PC}$ = 124.0 Hz), 144.1 (d, $^2J_{PC}$ 27.7 Hz), 191.2 ppm. $^{31}$P-NMR (121 MHz, CDCl$_3$) δ −143.6 (h, $^1J_{PF}$ 712.5 Hz), 76.2 ppm.<br>HRMS (ESI$^+$) [M]$^+$ calcd. for C$_{23}$H$_{31}$AuN$_2$PS$_3$, 659.1047; found, 659.1043. |
| FIG. 3 | [Gold(III) 2-((diisopropylamino)(phenyl)phosphorothioyl)phenyl) (piperidin-1-dithiocarbamate)] hexafluorophosphate<br>$^1$H NMR (600 MHz, DMSO-d$_6$) δ 1.17 (d, $^3J_{PH}$ 6.8 Hz, 6H), 1.26 (d, $^3J_{PH}$ 6.8 Hz, 6H), 1.71-1.75 (m, 6H), 3.75 (dh, $^2J_{HH}$ 18.2 Hz, $^3J_{HH}$ 6.8 Hz, 2H), 3.87-3.93 (m, 6H), 7.43-7.45 (m, 1H), 7.43-7.45 (m, 2H), 7.71-7.75 (m, 2H), 7.82 (td, 1H, $^3J_{HH}$ 7.4 Hz, $^4J_{HH}$ 1.7 Hz), 7.43-7.45 (m, 1H), 8.21-8.25 (m, 2H) ppm. $^{13}$C NMR (150 MHz, DMSO-d$_6$) 23.0 (d, $^3J_{PC}$ 3.0 Hz), 23.2 (d, $^3J_{PC}$ 3.2 Hz), 23.9, 25.6, 25.7, 50.7 (d, $^2J_{PC}$ 3.0 Hz), 51.0, 51.1, 127.8 (d, $^1J_{PC}$ 101.3 Hz), 128.9 (d, $^3J_{PC}$ 12.0 Hz), 130.1 (d, $^3J_{PC}$ 13.6 Hz), 132.8 (d, $^3J_{PC}$ 16.7 Hz), 133.8 (d, $^2J_{PC}$ 12.0 Hz), 134.2 (d, $^2J_{PC}$ 12.5 Hz), 135.3 (d, $^4J_{PC}$ 3.0 Hz), 136.0 (d, $^4J_{PC}$ 3.5 Hz), 139.0 (d, $^1J_{PC}$ = 123.7 Hz), 144.1 (d, $^2J_{PC}$ 28.0 Hz), 190.6 ppm. $^{31}$P-NMR (121 MHz, CD$_3$CN) δ −143.9 (h, $^1J_{PF}$ 706.2 Hz), 75.6 ppm.<br>HRMS (ESI$^+$) [M]$^+$ calcd. for C$_{24}$H$_{33}$AuN$_2$PS$_3$, 673.1204; found, 673.1244. |
| FIG. 4 | [Gold(III) 2-((diisopropylamino)(phenyl)phosphorothioyl)phenyl) (1-cyclopropyl-6-fluoro-4-oxo-7-(piperazin4-dithiocarbamate-1-il)-quinolin-3-carboxylic acid)] hexafluorophosphate<br>$^1$H NMR (600 MHz, DMSO-d$_6$) δ 1.17 (d, $^3J_{PH}$ 6.8 Hz, 6H), 1.26 (d, $^3J_{PH}$ 6.8 Hz, 6H), 1.71-1.75 (m, 6H), 3.75 (dh, $^2J_{HH}$ 18.2 Hz, $^3J_{HH}$ 6.8 Hz, 2H), 3.87-3.93 (m, 6H), 7.43-7.45 (m, 1H), 7.43-7.45 (m, 2H), 7.71-7.75 (m, 2H), 7.82 (td, 1H, $^3J_{HH}$ 7.4 Hz, $^4J_{HH}$ 1.7 Hz), 7.43-7.45 (m, 1H), 8.21-8.25 (m, 2H) ppm. $^{13}$C NMR (150 MHz, DMSO-d$_6$) 8.1, 23.0 (d, $^3J_{PC}$ 3.3 Hz), 23.2 (d, $^3J_{PC}$ 3.2 Hz), 48.8, 49.2, 49.4, 50.7 (d, $^2J_{PC}$ 2.9 Hz), 107.0, 111.8, 111.9, 127.5, 128.2, 129.0 (d, $^3J_{PC}$ 11.9 Hz), 130.1 (d, $^3J_{PC}$ 13.6 Hz), 132.8 (d, $^3J_{PC}$ 16.8 Hz), 133.8 (d, $^2J_{PC}$ 12.0 Hz), 134.2 (d, $^2J_{PC}$ 12.4 Hz), 135.3 (d, $^4J_{PC}$ 3.0 Hz), 136.2 (d, $^4J_{PC}$ 3.6 Hz), 138.8, 138.9 (d, $^1J_{PC}$ = 123.7 Hz), 144.1 (d, $^2J_{PC}$ 27.7 Hz), 147.8, 151.8, 153.4, 175.5, 166.8, 193.2 ppm. $^{31}$P-NMR (121 MHz, CD$_3$CN) δ −114.6 (h, $^1J_{PF}$ 713.2 Hz), 70.9, 76.2 ppm.<br>HRMS (ESI$^+$) [M]$^+$ calcd. for C$_{36}$H$_{40}$AuFN$_4$O$_3$PS$_3$, 919.1650; found, 919.1667. |

As representative examples, copies of NMR spectra for compounds 2b and 2g are shown in FIGS. 7 to 12: $^1$H— (FIG. 7), $^{13}$C— (FIG. 8), $^{31}$P (FIG. 9) NMR spectra of 2b; $^1$H— (FIG. 10), $^{13}$C— (FIG. 11), $^{31}$P (FIG. 12) NMR spectra of 2g.

X-Ray Diffraction

Figure 5:
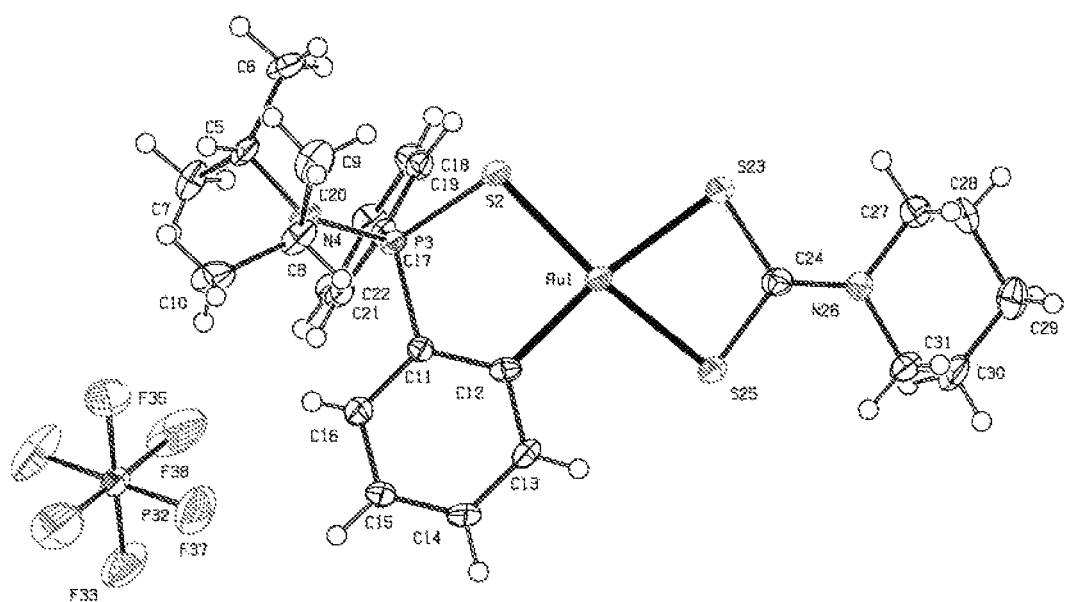
FIG. 5 is a view of the molecular structure of complex 2g, with partial atom labeling scheme and displacement ellipsoids drawn at 50% probability level.

Single crystal X-ray diffraction data were collected on a Bruker D8 Venture diffractometer at 100 K, using CuK$_\alpha$ radiation (λ=1.54178 Å). Data collection and cell refinement were performed with Bruker Instrument Service v4.2.2. Empirical multiscan absorption correction using equivalent reflections was performed with the SADABS program. The structure solution and full-matrix least-squares refinement based on F^2 was performed with CRYSTALS (Betteridge, P W, Carruthers, J R, Cooper, R I, Prout, K, Watkin, D J, J. Appl. Cryst. 2003 36, 1487). All atoms except for hydrogen were refined anisotropically. Hydrogen atoms were treated by a mixture of independent and constrained refinement. A summary of crystal data and refinement details for compound 2g are given in Table 2. FIG. 5 was drawn using the program PLATON. Selected bond-distances and bond angles are given in Table 3.

TABLE 2

| Bond precision: | C—C = 0.0077 A | | Wavelength = 1.54180 |
|---|---|---|---|
| Cell: | a = 13.2542(4) | b = 25.8434(7) | c = 8.9111(3) |
| | alpha = 90 | beta = 101.5753(13) | gamma = 90 |
| Temperature: | 100 K | | |

| | Calculated | Reported |
|---|---|---|
| Volume | 2990.27(16) | 2990.27(10) |
| Space group | P 21/c | P 1 21/c 1 |
| Hall group | -P 2ybc | ? |
| Moiety formula | C24 H33 Au N2 P S3, F6 P | C4 H5.50 Au0.17 F1 N0.33 P0.33 S0.50 |
| Sum formula | C24 H33 Au F6 N2 P2 S3 | C4 H5.50 Au0.17 F1 N0.33 P0.33 S0.50 |
| Mr | 818.61 | 136.44 |
| Dx, g cm-3 | 1.818 | 1.818 |
| Z | 4 | 24 |
| Mu (mm-1) | 12.719 | 12.719 |
| F000 | 1608.0 | 1608.0 |
| F000' | 1600.63 | |
| h, k, lmax | 15, 30, 10 | 15, 30, 10 |
| Nref | 4950 | 4937 |
| Tmin, Tmax | 0.433, 0.579 | 0.560, 0.760 |
| Tmin' | 0.201 | |

TABLE 2-continued

| Correction method = #Reported T Limits: Tmin = 0.560 Tmax = 0.760 AbsCorr = GAUSSIAN | | |
|---|---|---|
| Data completeness = 0.997 | Theta(max) = 63.813 | |
| R(reflections) = 0.0283 (4349) | wR2(reflections) = 0.0632 (4914) | |
| S = 0.985 | Npar = 443 | |

TABLE 3

| Bond lengths | | | |
|---|---|---|---|
| Au1-S2 | 2.330(11) | Au1-S25 | 2.317(12) |
| Au1-S23 | 2.058(18) | Au1-C12 | 2.058(5) |
| Bond angles | | | |
| S2-Au1-S23 | 97.64(4) | S2-Au1-C12 | 90.68(13) |
| S23-Au1-S25 | 74.99(4) | C12-Au1-S23 | 171.69(13) |
| S4-Au1-S25 | 172.42(4) | S2-Au1-C24 | 134.35(16) |

Stability Studies of the Gold (III) Complexes 2

Figure 13:
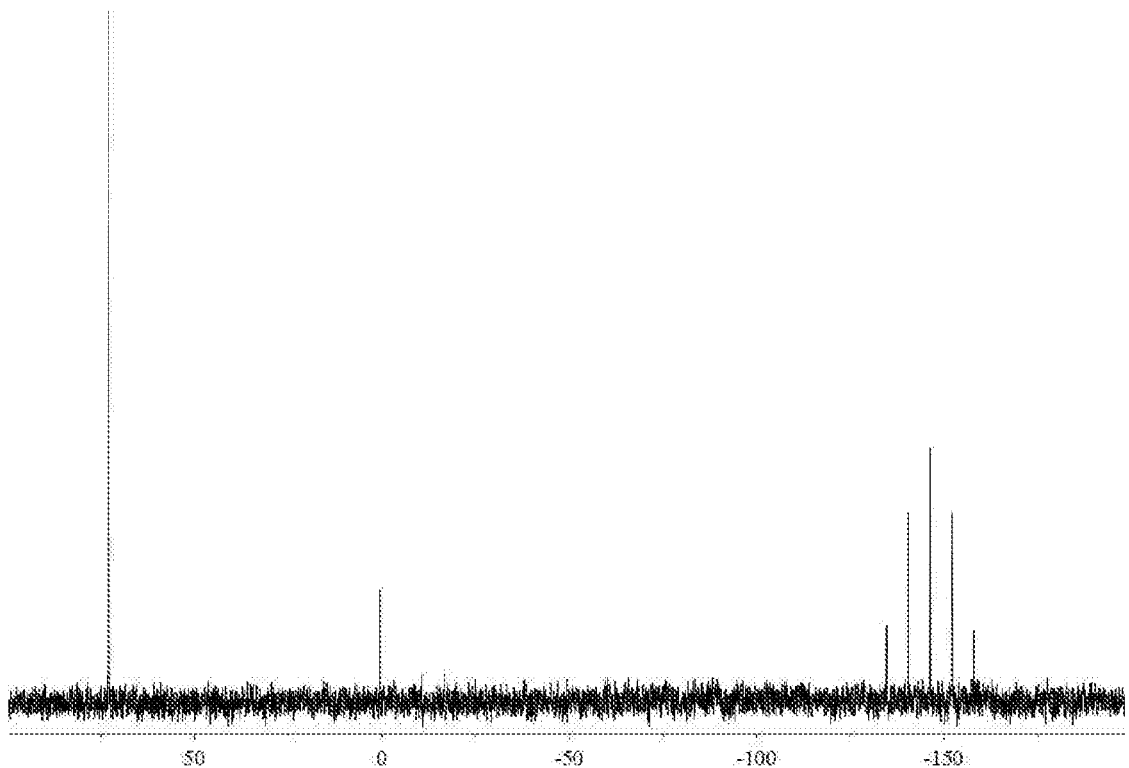
FIG. 13 is a $^{31}$P—NMR spectrum of complex 2f in 0.25 mL CD$_3$CN/0.25 mL of phosphate buffer, at 37° C., taken immediately after dissolution.
Figure 14:
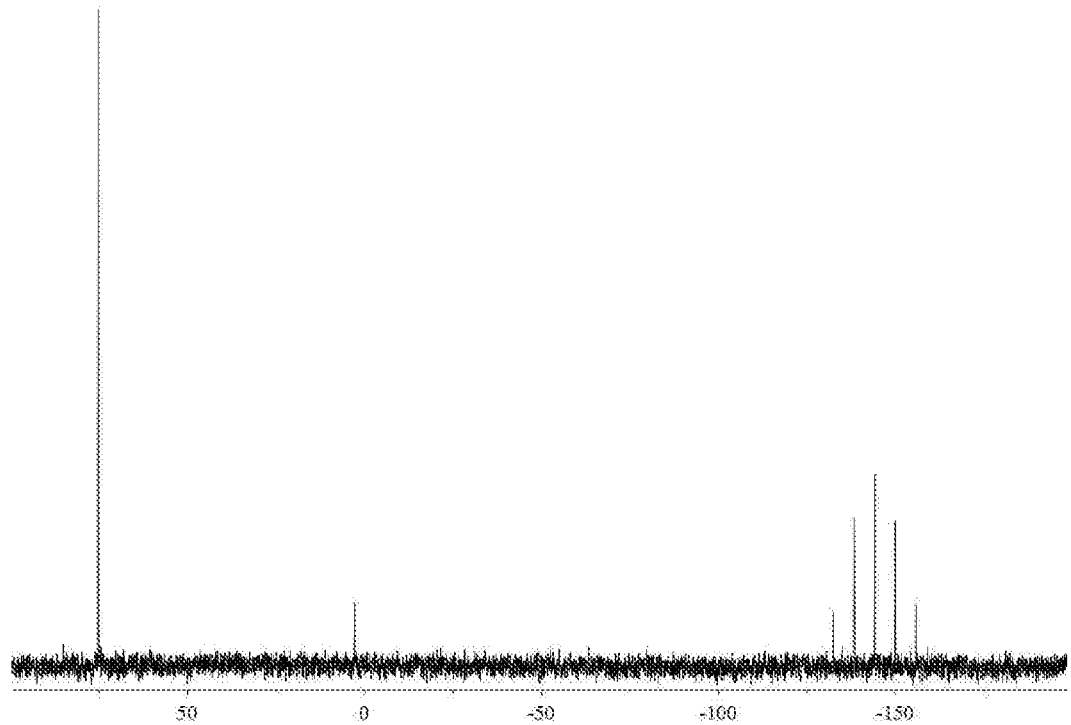
FIG. 14 is a $^{31}$P—NMR spectrum of complex 2f in 0.25 mL CD$_3$CN/0.25 mL of phosphate buffer, at 37° C., taken 3 days after dissolution.

A solution of compound 2f in $CD_3CN$ (0.25 mL) was mixed with 0.25 mL of saline phosphate buffer (pH 7.4) in $D_2O$ and the mixture was monitored at 37° C. over three days through $^1H$ and $^{31}P$ NMR spectroscopy. As illustrated in FIGS. 13 and 14, the $^{31}P$ NMR signal of the complex remained unaltered over the three-day period. Such observations show a substantial evidence for the stability of complexes 2 under physiological conditions.

Figure 15:
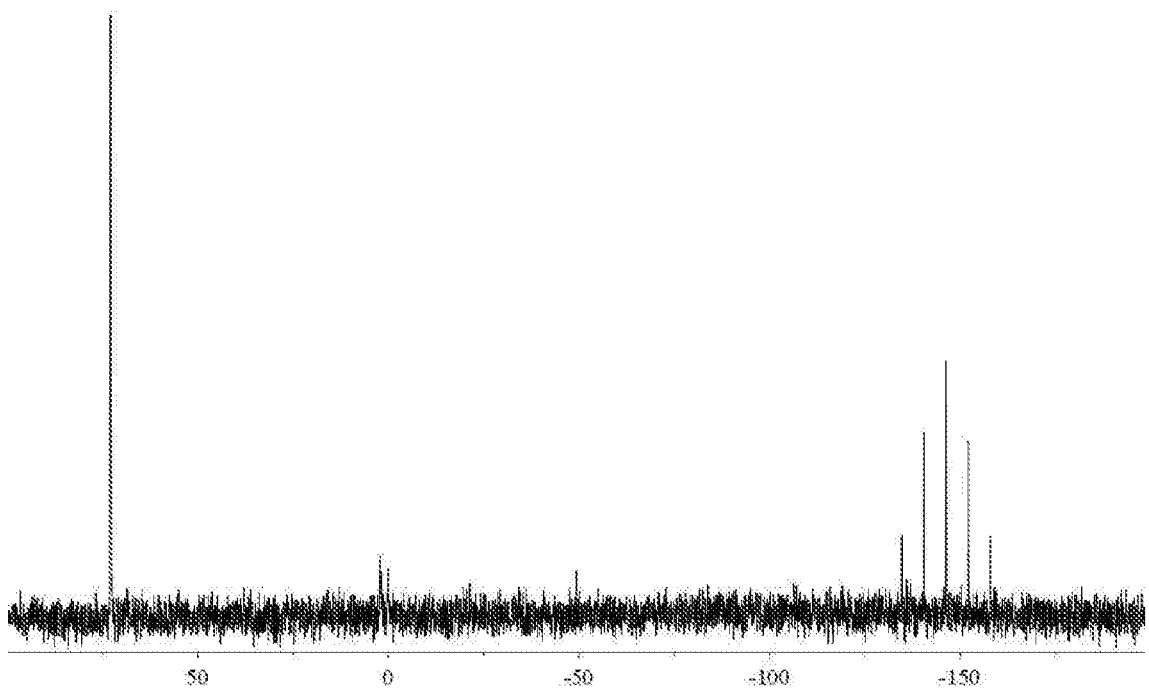
FIG. 15 is a $^{31}$P—NMR spectrum of complex 2f in 0.25 mL CD$_3$CN and ISO culture broth in 0.25 mL of D$_2$O.

Complexes 2 are also stable in the conditions used for the biological activity assays, as evidenced by the $^{31}P$ NMR spectra of a solution of compound 2f in $CD_3CN$ (0.25 mL) and 0.25 mL of ISOsensitest culture broth prepared in $D_2O$ (FIG. 15).

Figure 16:
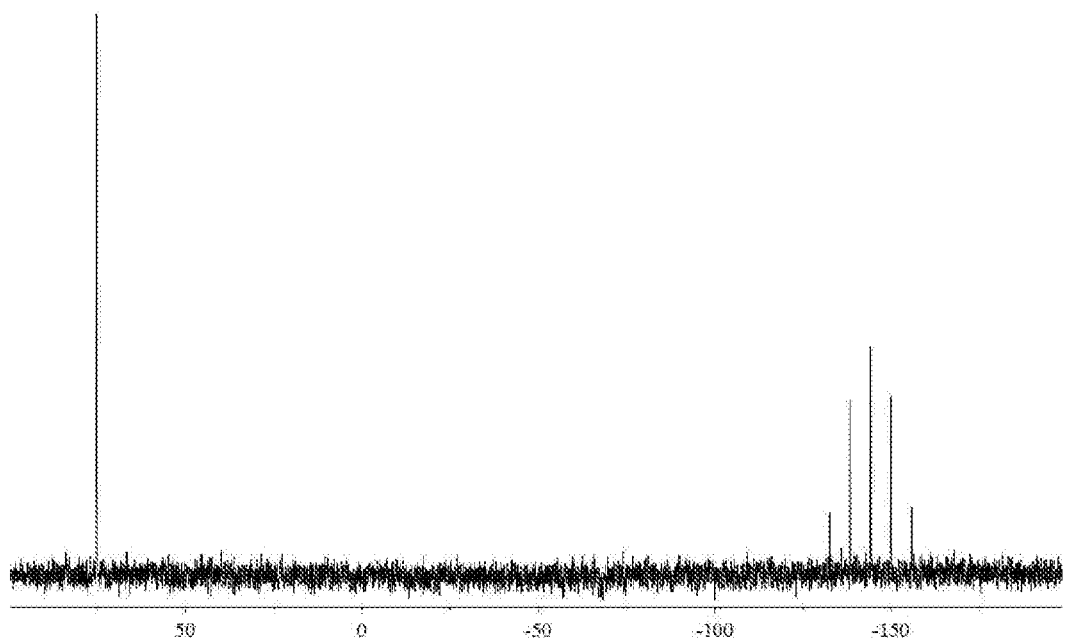
FIG. 16 is a $^{31}$P—NMR spectrum of complex 2f in 0.25 mL CD$_3$CN and 1 equiv. of glutathione in 0.25 mL of H$_2$O.
Figure 17:
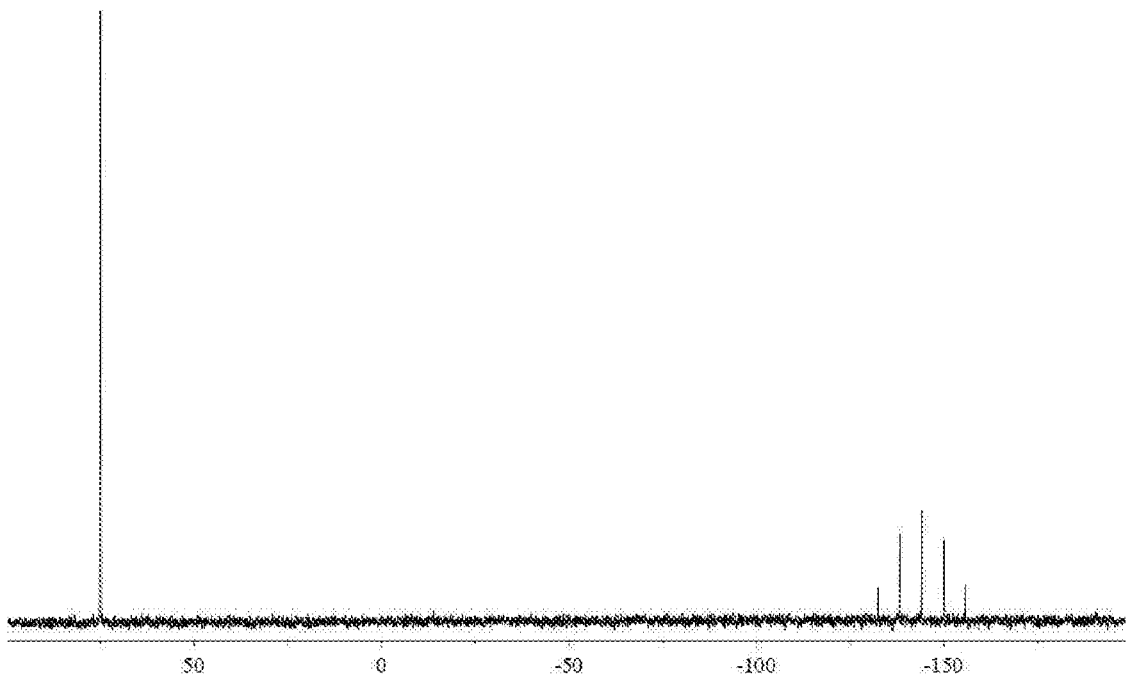
FIG. 17 is a $^{31}$P—NMR spectrum of complex 2f in 0.25 mL CD$_3$CN and 1 equiv. of ascorbic acid in 0.25 mL of H$_2$O.

To gain a more complete picture of the stability and the solution behavior of these gold(III) compounds 2, the spectral changes produced by addition of classical reducing agents, i.e. glutathione (GSH) and ascorbic acid (AsAc) were also examined. Thus, solutions of compound 2f in $CD_3CN$ (0.25 mL) were mixed with solutions containing equimolar amounts of either GSH or AsAc in 0.25 mL of $H_2O$. The $^{31}P$ NMR spectra clearly indicated that the gold complex maintained its chemical integrity, as evidenced by the NMR spectra presented in FIGS. 16 and 17.

Example 2

Antimicrobial Activity

| Strain | Resistance profile | MIC formula (I) (mg/L) | MIC Ciprofloxacin (Cip) (mg/L) | MIC Levofloxacin (Lvx) (mg/L) |
|---|---|---|---|---|
| MRSA 1 | Cip, Cli, Eri, Pen, Lvx | 0.25 | 128 | 128 |
| MRSA 2 | Gen, Cip, Cli, Eri, Pen, Lvx | 0.25 | 16 | 64 |

MRSA methicillin resistant S. aureus;
Cip, ciprofloxacin;
Cli, clindamycin;
Eri, erithromycin;
Pen, penicillin;
Lvx, levofloxacin;
Gen, gentamicin.

This example evidenced the high antibacterial activity shown by the compound of formula (I) in comparison with Cip and Lvx, both antimicrobial agents used in the treatment of infection caused by MRSA. The compounds are active at concentrations until 9-fold lower (MIC 128 mg/L for Cip in contrast to 0.25 mg/L for formula (I) compound) than these antimicrobial agents.

Example 3

In Vivo Toxicity Assay

Treatment: Single intravenous dose (100 pL) of 2-10 mg/kg of the compounds 2 (or formula (I)) and vehicle control groups DMSO.

Development: The animals were monitored for 2 weeks after the inoculation of the treatment. Signs of toxicity such as weight reduction, bristly coat, reduced mobility, ocular epiphora were verified. The animals were weighed each day until the end of the experiment. A decrease of 80% of the initial weight of the mouse was considered as an endpoint criterion.

Figure 6:
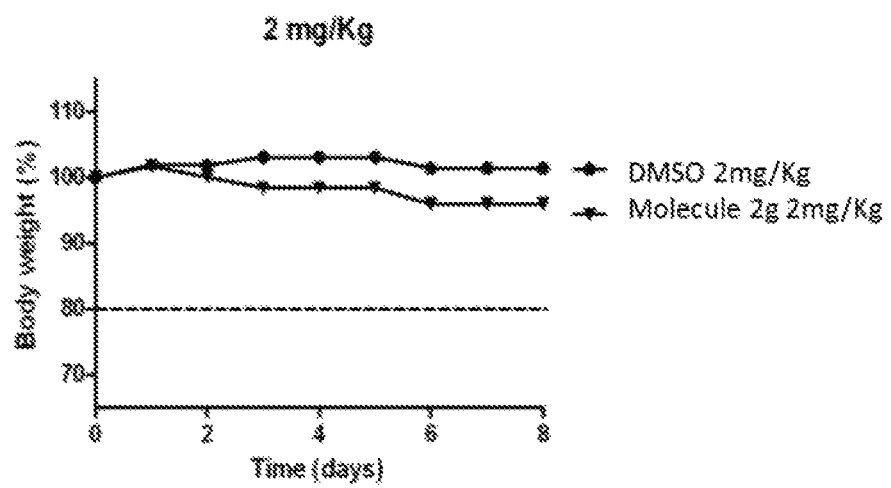
FIG. 6 is a graph showing the toxicity of 2g.
Figure 7:
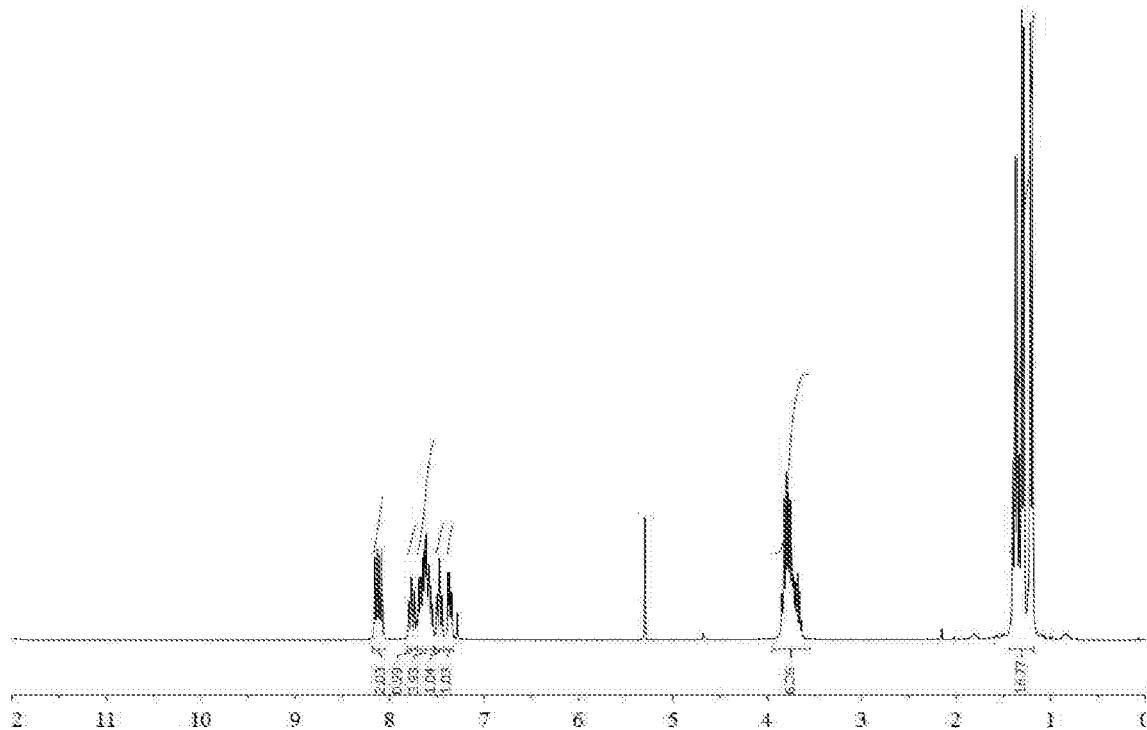
FIG. 7 is a $^1$H—NMR spectrum of complex 2b
Figure 8:
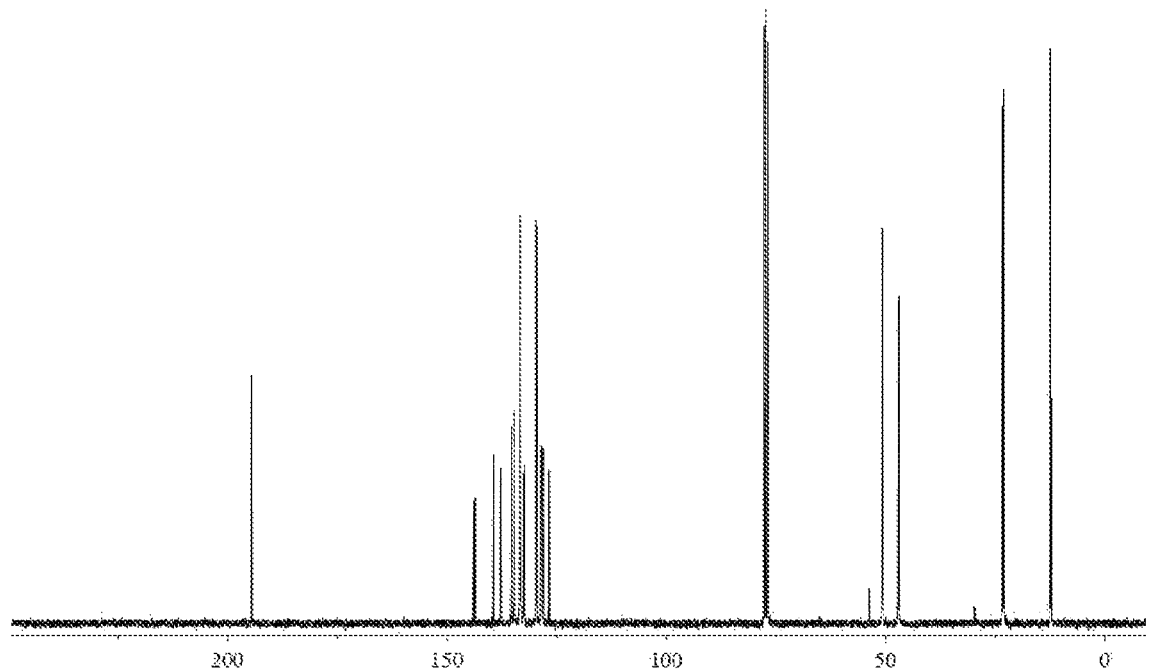
FIG. 8 is a $^{13}$C—NMR spectrum of complex 2b
Figure 9:
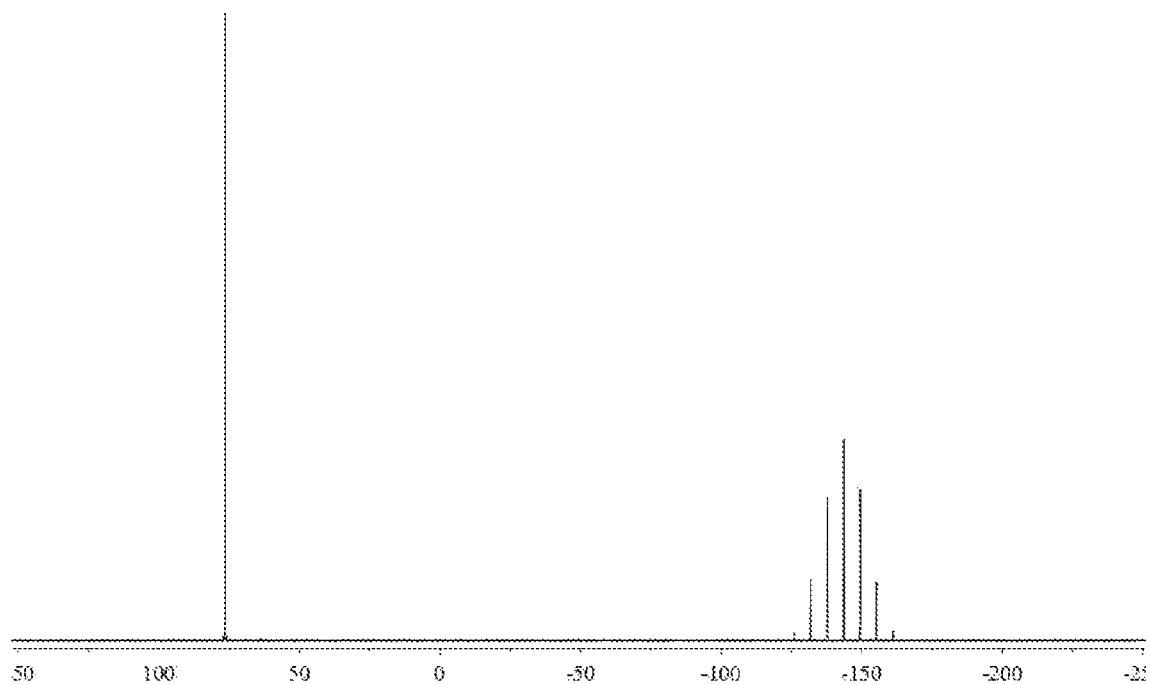
FIG. 9 is a $^{31}$P—NMR spectrum of complex 2b
Figure 10:
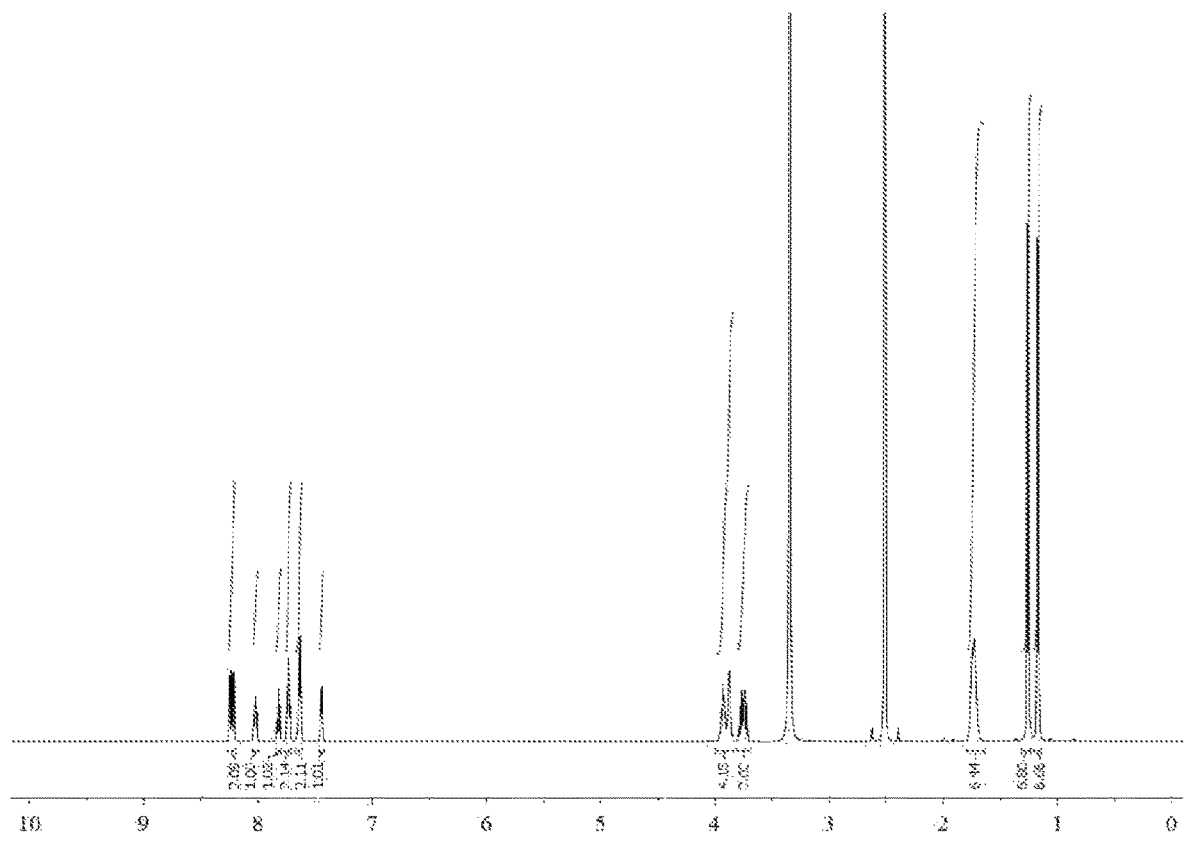
FIG. 10 is a $^1$H—NMR spectrum of complex 2g
Figure 11:
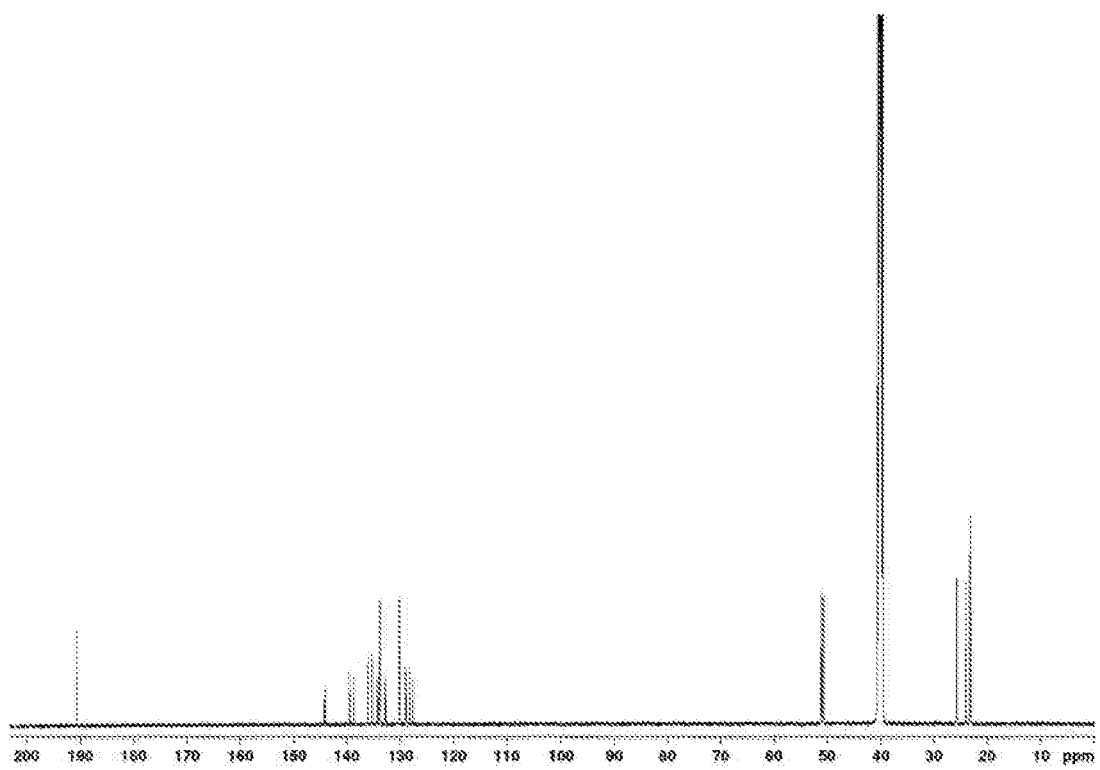
FIG. 11 is a $^{13}$C—NMR spectrum of complex 2g
Figure 12:
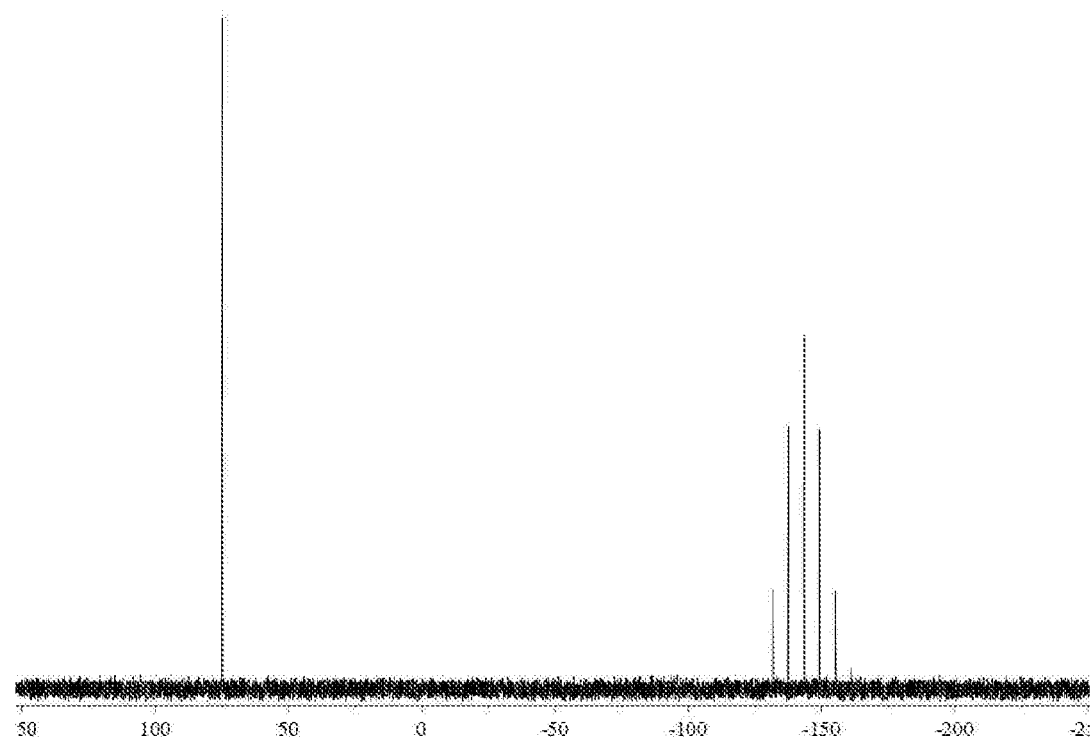
FIG. 12 is a $^{31}$P—NMR spectrum of complex 2g

Result: No significant differences in weight were observed in the dose of 2 mg/kg of the molecule with respect to the control group, see FIG. 6.

Example 4. Antibiofilm Activity

| Strain | Resistance profile | MBIC formula (I) (mg/L) | MBIC Ciprofloxacin (Cip) (mg/L) | MBIC Levofloxacin (Lvx) (mg/L) |
|---|---|---|---|---|
| MRSA 1 | Cip, Cli, Eri, Pen, Lvx | 1 | 256 | >256 |
| MRSA 2 | Gen, Cip, Cli, Eri, Pen, Lvx | 1 | 256 | 128 |

MRSA methicillin resistant S. aureus;
Cip, ciprofloxacin;
Cli, clindamycin;
Eri, erithromycin;
Pen, penicillin;
Lvx, levofloxacin;
Gen, gentamicin.

This example evidenced the high antibiofilm activity shown by the compound of formula (I) in comparison with Cip and Lvx. The compounds are active at concentrations until 8-fold lower (MIC 256 mg/L for Cip in contrast to 1 mg/L for formula(I) compound) than these antimicrobial agents.

Besides the above examples and results, the proposed gold(III) complex has also showed a synergistic effect with colistine. The minimal inhibitory concentrations of the combination of the gold(III) complex and colistine in Gram-negative are significantly lower than those obtained with each antibiotic separately. Thus, the MIC of the gold(III) complex for A. baumannii is 4 mg/L and the MIC for colistine is 64 mg/L. However, when they are used in combination, the MICs of each antibiotic decrease to 0.25 and 1 mg/L, respectively.

Also, a susceptible strain of MRSA was submitted to different concentrations of the gold(III) complex during 30 days. Each day, the tube showing bacterial growth was spread into an agar plate and the colonies were tested for their resistance to the gold(III) complex. Daptomycin was used as control of acquisition of resistance. The experiment was made by duplicate. After the 30 days, no increase in the MIC was found. Therefore, the gold(III) complex does not generate resistance.

An in vitro toxicity assay has been also made. Jurkat E6.1 cells were exposed to different concentrations of the gold (III) complex. The IC50, the concentration that kill the 50% of the cells was calculated. The gold(III) complex presented a IC50 of 3.77 mg/L. Taking into account that the MIC for MRSA is 0.06-0.5 mg/L, this toxicity value is included in the range of non-toxic.

The time of which the gold(III) complex kill all the bacteria was also calculated. Other antibiotics were used as controls. The molecule kills all the bacteria at 2×MIC in 4-8 hours.

The effectiveness of the gold(III) complex for treating a bacterial infection was tested too. An infection model of sepsis by *S. aureus* was established. The clinical strain S54F9 was used for the infection. 6×10⁶ cfu/mice was inoculated. Three groups of 5 mice were used>: i) control: mice infected but no-treated; ii) mice treated with a single dose of 5 mg/kg; iii) mice treated with multiple doses of 5 mg/kg each 24 h. The mice of the control group died after 48 h post-inoculation. The mice of the single doses group died after 5 days post-inoculation. The mice of the multiple doses group died after 4 days post-inoculation.

The above describes embodiments of the present invention; modifications obvious to those skilled in the art can be made thereto without departing from the scope of the present invention.

The scope of the present invention is defined in the following set of claims.

The invention claimed is:

1. A pharmaceutically acceptable salt of a gold(III) complex, having formula (I):

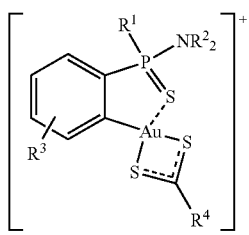

wherein:
R¹ is independently selected from aryl and amine;
R² is independently selected from alkyl and cycloalkyl;
R³ is independently selected from hydrogen, halogen, nitro, cyano, alkyl, alkyloxy, alkylamino, aminodialkyl, hydroxyalkyl, trialkylsilyl, aryldialkylsilyl, alkylthio, cycloalkyl, aryl, heterocycle, polycycle, amino acid, and peptide; and
R⁴ is independently selected from alkyl, cycloalkyl, alkylalkoxy, alkylamino, dialkylamino, aliphatic amine, alkylthio, trialkylphosphino, dialkylarylphosphino, alkyldiarylphosphino, triarylphosphino, aryl, heterocycle, polycycle, amino acid and peptide.

2. The pharmaceutically acceptable salt of a gold(III) complex of claim 1, wherein R¹ is a phenyl; R² is an alkyl or a cycloalkyl; R³ is an hydrogen; and R⁴ is an aliphatic amine.

3. The pharmaceutically acceptable salt of a gold(III) complex of claim 2, wherein the aliphatic amine is NMe₂, NEt₂, N(CH₂Ph)₂, pyrrolidyl, piperidinyl, and azepanyl, or heterocycle.

4. A pharmaceutical composition consisting of the pharmaceutically acceptable salt of a gold(III) complex of claim 1 and at least one pharmaceutically acceptable excipient.

5. A process for preparing the pharmaceutically stable salt of a gold(III) complex of claim 1, comprising reacting a compound of formula (V)

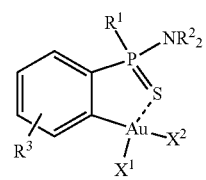

with a compound of formula (VI)

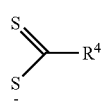

and subsequent formation of a pharmaceutically stable salt of the resulting complex by treatment with an organic or inorganic acid or their corresponding salts, wherein:
X¹ is independently selected from halogen, hydroxide or acetoxy;
X² is independently selected from halogen, hydroxide or acetoxy;
R¹ is independently selected from aryl and amine;
R² is independently selected from alkyl and cycloalkyl;
R³ is independently selected from hydrogen, halogen, nitro, cyano, alkyl, alkyloxy, alkylamino, aminodialkyl, hydroxyalkyl, trialkylsilyl, aryldialkylsilyl, alkylthio, cycloalkyl, aryl, heterocycle, polycycle, amino acid, and peptide; and
R⁴ is independently selected from alkyl, cycloalkyl, alkylalkoxy, alkylamino, dialkylamino, aliphatic amine, alkylthio, trialkylphosphino, dialkylarylphosphino, alkyldiarylphosphino, triarylphosphino, aryl, heterocycle, polycycle, amino acid, and peptide.

6. The process of claim 5, wherein R¹ is a phenyl; R² is an alkyl or a cycloalkyl; R³ is a hydrogen; and R⁴ is an aliphatic amine.

* * * * *